United States Patent [19]

Kallenbach et al.

[11] Patent Number: 5,349,116
[45] Date of Patent: Sep. 20, 1994

[54] ALKANE ALKYLATION AND CATALYST THEREFOR

[75] Inventors: Lyle R. Kallenbach; Marvin M. Johnson, both of Bartlesville, Okla.

[73] Assignee: Phillips Petroleum Company, Bartlesville, Okla.

[21] Appl. No.: 82,586

[22] Filed: Jun. 25, 1993

[51] Int. Cl.$^5$ ................................................ C07C 2/62
[52] U.S. Cl. .................... 585/730; 585/720; 585/721; 502/20
[58] Field of Search ............ 585/720, 721, 730; 502/20

[56] References Cited

U.S. PATENT DOCUMENTS

| | | | |
|---|---|---|---|
| 3,844,931 | 10/1974 | Ishiguro et al. | 208/46 |
| 3,887,635 | 6/1975 | Parker et al. | 260/683.47 |
| 4,065,516 | 12/1977 | Moser, Jr. et al. | 260/683.47 |
| 5,220,095 | 6/1993 | Hommeltoft et al. | 585/720 |
| 5,233,119 | 8/1993 | Kallenbach et al. | 585/721 |

FOREIGN PATENT DOCUMENTS 0433954 6/1991 European Pat. Off. .

OTHER PUBLICATIONS

M. C. Tsai and Y. W. Yen, "Hydrothermal Stability of Aluminum Borate", Catalysis Letters 6 (1990), pp. 225–230.

*Primary Examiner*—Asok Pal
*Attorney, Agent, or Firm*—K. K. Brandes

[57] ABSTRACT

A composition of matter comprises trifluoromethanesulfonic acid and a solid inorganic material which contains aluminum borate and aluminum oxide, This composition is used as a catalyst for alkylating at least one $C_2$-$C_{10}$ alkane (preferably isobutane and/or an isooctane) with at least one $C_2$-$C_{10}$ alkene (preferably pentene-1 and/or hexene-1).

20 Claims, No Drawings

ALKANE ALKYLATION AND CATALYST THEREFOR

BACKGROUND OF THE INVENTION

In one aspect, this invention relates to a novel composition of matter, which is effective as an alkylation catalyst, comprising trifluoromethanesulfonic acid and an inorganic solid support material. In another aspect, this invention relates to the alkylation of alkanes (paraffins) with alkenes (monoolefins), in the presence of a novel solid catalyst composition comprising trifluoromethanesulfonic acid and a solid support material.

The use of supported trifluoromethanesulfonic acid catalysts for the alkylation of alkanes with alkenes is known and has been described in the patent literature, e.g., in European Patent Application having Publication No. EP 0 433 954 A1). The present invention is directed to a novel, effective alkylation catalyst composition comprising trifluoromethanesulfonic acid and a specific inorganic support material, and to the use of said catalyst composition in an alkylation process.

SUMMARY OF THE INVENTION

It is an object of this invention to provide a novel composition of matter which is active as an alkylation catalyst. It is another object of this invention to alkylate alkanes with alkenes in the presence of a novel catalyst comprising trifluoromethanesulfonic acid and a solid inorganic material. Other objects and advantages will be apparent from the detailed description of the appended claims.

In accordance with this invention, a composition of matter (effective as a catalyst for alkylating alkanes with alkenes) comprises trifluoromethanesulfonic acid and a solid material comprising aluminum borate and aluminum oxide. Preferably, this composition of matter consists essentially of trifluoromethanesulfonic acid, aluminum borate and aluminum oxide. In a more preferred embodiment, the composition of matter of this invention consists essentially of trifluoromethanesulfonic acid, coprecipitated aluminum borate/oxide having a B:Al atomic ratio of about 0.4:1 to about 4:1, and alumina (on which coprecipitated Al borate/oxide is deposited).

Further in accordance with this invention, a process for alkylating alkanes comprises the step of contacting at least one feed alkane (i.e., at least one straight-chain alkane or at least one branched alkane or a mixture thereof) containing about 2–10 carbon atoms per molecule with at least one feed alkene (i.e., at least one straight-chain alkene or at least one branched alkene or a mixture thereof) containing about 2–10 carbon atoms per molecule with the above-described catalyst composition comprising trifluoromethanesulfonic acid, aluminum borate and aluminum oxide at effective alkylation conditions and to produce at least one product alkane containing at least two more carbon atoms per molecule than said at least one feed alkane.

DETAILED DESCRIPTION OF THE INVENTION

The composition of matter of this invention comprises $CF_3SO_3H$ on (b) a solid inorganic material which contains aluminum borate and aluminum oxide. Generally, the solid inorganic material (b) contains about 5 to about 15 weight-% aluminum borate, and aluminum oxide as the remainder, preferably about 7–13 weight-% Al borate and about 87–93 weight-% Al oxide. Preferably, the solid inorganic material is a coprecipitate of aluminum borate and aluminum oxide supported by alumina particles, i.e., alumina particles which are coated with a coprecipitate of Al borate and Al oxide. The BET/$N_2$ surface area of this solid inorganic material generally is in the range of about 200 to about 400 $m^2/g$. Preferably, the particles of the composition of matter have a size in the range of about 0.4 mm to about 3.2 mm (i.e., smaller than about 6 mesh and larger than about 40 mesh).

The composition of matter of this invention can be prepared in any suitable manner. Preferably, the solid inorganic material is prepared by mixing boric acid ($H_3BO_3$), at least one water-soluble aluminum salt (i.e., one or two or more than two Al salts, preferably aluminum nitrate) and water. Preferably, the molar ratio of the boric acid to the at least one aluminum salt in the resulting aqueous solution is in the range of about 0.03:21 to about 15:1, more preferably about 0.4:1 to about 4:1. This aqueous solution of dissolved $H_3BO_3$ and dissolved Al salt is then mixed with alumina support particles. An aqueous solution of ammonia is added to the thus-obtained aqueous slurry in an amount required to attain a pH of about 7–8, resulting in the formation of a coprecipitate of aluminum borate and aluminum oxide on alumina support particles, wherein the formed solids are dispersed in the aqueous phase having a pH of about 7–8. Generally, the weight ratio (on a dry basis) of alumina support particles to coprecipitated Al borate/oxide is about 5:1 to about 20:1. The formed combination of coprecipitated Al borate/oxide and alumina support particles which is dispersed in the aqueous phase is then separated from the aqueous phase of the dispersion, preferably by draining or filtration, followed by washing with water (preferably deionized or distilled water). The thus-obtained solid inorganic material is then generally dried (preferably for about 0.1–20 hours at a temperature of about 100°–150° C.) and calcined (preferably for about 2–6 hours at a temperature of about 450°–600° C., more preferably about 480°–570° C., either in air or in a $N_2$ atmosphere). The $CF_3SO_3H$ catalyst component can be applied to this solid inorganic material in any suitable manner. Generally, it is added in liquid form to the top layer of the solid inorganic support material (preferably being present in a catalyst bed) just prior to the alkylation reaction, generally at a weight ratio of $CF_3SO_3H$ to said solid inorganic material in the range of about 0.02:1 to about 0.4:1.

The composition or matter described above is employed as catalysts in the alkylation process of this invention. The process for alkylating $C_2$-$C_{10}$ alkanes (preferably isoalkanes, i.e., branched alkanes) with $C_2$-$C_{10}$ alkenes (preferably those containing an internal double bond) can be carried out in any suitable manner. The contacting of a mixture of at least one feed alkane and at least one feed alkene, generally at a molar alkane-/alkene ratio of about 6:1 to about 12:1 (preferably about 8:1 to about 10:1), with the above-described catalyst compositions can be carried out at effective alkylation conditions, generally at a relatively low temperature of up to about 100° C., preferably about −20° to about 100° C., more preferably about 0°–30° C., generally at an absolute pressure of about 2–8 atm (equivalent to about 15–103 psig).

The alkane/alkene feed mixture can be contacted with the catalyst composition in any suitable mode, preferably in a fixed catalyst bed operation in which the feed mixture flows downward through a solid catalyst layer, generally at a liquid hourly space velocity of about 0.5–5 (preferably about 1–3) cm$^3$ alkane/alkene feed per cm$^3$ catalyst composition per hour. The alkylation process can be carried out in a continuous manner or as a batch process. Generally, the CF$_3$SO$_3$H component moves as a zone along the solid catalyst bed in the direction of the alkylation feed. When the CF$_3$SO$_3$H zone approaches the exit region of the catalyst bed, the reactant flow can be reversed (so that the CF$_3$SO$_3$H zone can travel back through the catalyst bed).

Suitable feed alkanes are normal (straight-chain) alkanes and isoalkanes (i.e., branched) alkanes, each containing 2–10 carbon atoms per molecule. Non-limiting examples of suitable alkanes are propane, n-butane (i.e., normal-butane), isobutane, n-pentane, isopentanes (2-methylbutane and 2,2-dimetbylpropane), n-hexane, isohexanes (such as 2-methylpentane, 3-methylpentane, 2,2-dimethylbutane), n-heptane and isoheptanes (such as methyl-substituted hexanes and dimethyl-substituted pentanes), n-octane, isooctanes, n-nonane, isononanes, n-decane and isodecanes. Presently preferred are C$_4$-C$_8$ alkanes. Particularly preferred feed alkanes are isobutane, 2,2,4- trimethylpentane and mixtures thereof.

Suitable feed alkenes are normal (straight chain) and branched alkenes containing one C=C double bond and 2–10 carbon atoms per molecule. Non-limiting examples of suitable alkenes are propylene, butene-1, butene-2, isobutylene (isobutene), pentene-1, pentene-2, isopentenes, hexene-1, hexene-2, hexene-3, isohexenes, n-heptenes, isoheptenes, n-octenes, isooctenes, n-nonenes, isononenes, n-decenes and isodecenes. Preferred alkenes are those containing 4–6 carbon atoms per molecule. Particularly, preferred feed alkenes are pentene-1, hexene-1 and mixtures thereof.

The alkylation process of this invention generally generates a multitude of hydrocarbon products containing a greater number of carbon atoms per molecule than the feed alkane(s), as is demonstrated in the examples. Thus, it is generally necessary to separate various hydrocarbon product fractions from one another and from unconverted feed hydrocarbons. This separation can be carried out in any suitable manner, generally by fractional distillation, as can easily be determined by persons skilled in the various liquid-liquid separation technologies. In a preferred embodiment, the more desirable alkanes, which are useful as solvents and have a boiling range of about 310°–500° F. (at atmospheric pressure conditions), are separated from undesirable oil hydrocarbons boiling above 500° F. and, preferably, also from unconverted feed hydrocarbons.

The following examples are provided to further illustrate the processes of this invention, and are not to be construed as unduly limiting the scope of this invention.

EXAMPLE I

This example illustrates the preparation of various solid inorganic support materials for catalysts comprising trifluoromethanesulfonic acid (abbreviated: triflic acid) and these inorganic support materials.

Catalyst Support A (Control) was a commercial spherical alumina material having been provided by Aluminum Company of America, Pittsburgh, Pa., under the product designation of S-100, having an average particle size of about ⅛ inch, and containing primarily pores in the 30–80 angstrom range. This alumina material was dried about 4 hours at 500° C. (932° F.) in a nitrogen gas atmosphere. The dried alumina particles were then placed in a flow reactor tube, and triflic acid was added just before the start of alkylation tests, as is described in Example II.

Catalyst Support B1 (Invention) contained aluminum borate and alumina. This material was prepared as follows. An aqueous solution of 25.50 g (0.412 mole) of H$_3$BO$_3$ and an aqueous solution of 43.12 g (0.115 mole) of Al(NO$_3$)$_3$.9H$_2$O were combined, and the combined solution was poured onto 75 g of S-100 alumina (described above). Then enough of a concentrated aqueous solution of NH$_3$ was added (with stirring) to the formed slurry (total volume: about 1.5 liter) until a final pH of 8.0 of the aqueous phase was attained. The resulting aqueous slurry of coprecipitated Al borate/oxide (having an approximate atomic B:Al ratio of 3.59:1) deposited on S-100 alumina was filtered, and the filter cake was washed with deionized water and then substantially dried (at about 120°–150° C.). The dry solid material was calcined for about 4 hours at about 500° C. in a nitrogen gas atmosphere. Thereafter, triflic acid was added to the calcined solid material, as is described in Example II.

Catalyst Support B2 (Invention) was prepared essentially in accordance with the procedure for Catalyst B1, except that 5.50 g (0.089 mole) of H$_3$BO$_3$ and 78.32 g (0.209 mole) of Al(NO$_3$)$_3$.9H$_2$O were used, thus resulting in a coprecipitated Al borate/oxide having an approximate B:Al atomic ratio 0.43:1.

Several other catalyst supports, which were not used for making alkylation catalysts, were also prepared substantially in accordance with the procedure for Catalyst Support B1, except that the atomic B:Al ratio of the Al borate/oxide coprecipitate was about 34.85:1, 8.44:1, 1.55:1 and 0.035:1, respectively. These atomic ratios were attained by the appropriate amounts of H$_3$BO$_3$ and Al(NO$_3$)$_3$.9H$_2$O, both dissolved in water, and adding concentrated aqueous NH$_3$ to the combined solutions of H$_3$BO$_3$ and Al(NO$_3$)$_3$.H$_2$O so as to afford the Al borate/oxide coprecipitate in the presence of S-100 alumina particles.

EXAMPLE II

This example illustrates the use of the catalysts supports described in Example I for making and using alkylation catalysts. A U-shaped stainless steel reactor tube (inner diameter: 0.29 inch; length: 60 inches) was filled with about 40–50 grams of catalyst supports A, B1 and B2. About 2.0 cm$^3$ of trifluoromethanesulfonic acid was then added to the top (entrance) zone of the packed column while N$_2$ gas passed through the column. The entire column was maintained at a temperature of about 64° F. A liquid alkylation feed containing 1465 g isobutene, 170 g of isooctane (2,2,4-trimethylpentane) and 170 g of hexene-1 or pentene-1 was pumped through the packed column at a rate of 1 cm$^3$ per minute. The exiting alkylation produce obtained at a reaction temperature of about 64° F. and a reaction pressure of about 100 psig, was analyzed about every 2 hours by means of a gas chromatograph and by simulated distillation (at atmospheric pressure), Each test, lasted about 20 hours. Average test results are summarized in Table I.

TABLE I

| Feed | Catalyst Support | Alkylation Product | | |
|---|---|---|---|---|
| | | Wt-% of $C_9$ + Hydrocarbons[1] | Wt-% of Fraction Boiling at 310–500° F. | Wt-% of Fraction Boiling above 500° F. |
| Isobutane/ Isooctane/ Hexene-1 | A (Control)[2] | 23 | 18 | 22 |
| Isobutane/ Isooctane/ Hexene-1 | A (Control)[2] | 35 | 16 | 23 |
| Isobutane/ Isooctane/ Hexene-1 | A (Control)[2] | 32 | 16 | 24 |
| Isobutane/ Isooctane/ Hexene-1 | B2 (Invention)[2] | 28 | 13 | 1 |
| Isobutane/ Isooctane/ Hexene-1 | B2 (Invention)[2] | 22 | 14 | 1 |
| Isobutane/ Isooctane/ Hexene-1 | B2 (Invention)[2] | 32 | 11 | 2 |
| Isobutane/ Isooctane/ Hexene-1 | B2 (Invention)[2] | 30 | 11 | 2 |
| Isobutane/ Isooctane/ Hexene-1 | B2 (Invention)[3] | 31 | 10 | 4 |
| Isobutane/ Isooctane/ Hexene-1 | B2 (Invention)[3] | 30 | 10 | 2 |
| Isobutane/ Isooctane/ Hexene-1 | B2 (Invention)[3] | 28 | 9 | 3 |
| Isobutane/ Isooctane/ Hexene-1 | B2 (Invention)[3] | 27 | 10 | 2 |
| Isobutane/ Isooctane/ Hexene-1 | B2 (Invention)[3] | 27 | 10 | 3 |
| Isobutane/ Isooctane/ Pentene-1 | B1 (Invention)[2] | 30 | 21 | 10 |
| Isobutane/ Isooctane/ Pentene-1 | B1 (Invention)[2] | 23 | 20 | 14 |

[1] determined by gas chromatography
[2] particle size: 6–8 mesh
[3] particle size: 20–40 mesh Test results summarized in Table I clearly demonstrate that the alkylation product obtained with the catalysts system of this invention (i.e., triflic said on coprecipitated Al borate/oxide and alumina) contained less of undesirable oily products boiling above 500° F. (at atmospheric pressure) than the product obtained with triflic acid on alumina as the catalyst.

Reasonable variations, modifications and adaptations for various usages and conditions can be made within the scope of the disclosure and the appended claims, without departing from the scope of this invention.

That which is claimed is:

1. A process for alkylating alkanes which comprises contacting at least one feed alkane containing about 4–8 carbon atoms per molecule with at least one feed alkene containing about 4–6 carbon atoms per molecule in the presence of a catalyst composition which consists essentially of (a) trifluoromethanesulfonic acid and (b) a solid inorganic material consisting essentially of aluminum borate and aluminum oxide, at effective alkylation conditions comprising a reaction temperature of up to about 100° C., so as to obtain a product in which the weight percentage of product alkanes boiling in a temperature range of about 310° F. to about 500° F. at atmospheric pressure conditions exceeds the weight percentage of product hydrocarbons boiling at a temperature above 500° F. at atmospheric pressure conditions.

2. A process in accordance with claim 1, wherein the weight ratio of trifluoromethanesulfonic acid to said solid inorganic material in said catalyst composition is in the range of about 0.02:1 to about 0.4:1.

3. A process in accordance with claim 2, wherein said solid inorganic material contains about 5–15 weight-% aluminum borate.

4. A process in accordance with claim 3, wherein said solid inorganic material is an alumina-supported coprecipitate of aluminum borate and aluminum oxide.

5. A process in accordance with claim 4 wherein said coprecipitate has a boron:aluminum atomic ratio of about 0.4:1 to about 4:1.

6. A process in accordance with claim 5, wherein said solid inorganic material has been prepared by a method comprising the steps of forming an aqueous solution of boric acid and at least one water-soluble aluminum salt wherein the molar ratio of boric acid to said at least one aluminum salt is in the range of about 0.03:1 to about 15:1, mixing said aqueous solution with alumina particles so as to form an aqueous slurry, adding an aqueous solution of ammonia to said aqueous slurry so as to attain a pH of about 7–8 of the aqueous phase of said aqueous slurry and to form a solid combination of a coprecipitate of (i) aluminum borate and aluminum oxide and (ii) alumina support particles wherein said solid combination is dispersed in said aqueous phase, separating said solid combination from said aqueous phase washing said solid combination with water, drying the obtained washed solid combination, and calcining the dried solid combination at a temperature of about 450°–600° C.

7. A process in accordance with claim 1, wherein said feed alkane is selected from the group consisting of isobutane and 2,2,4- trimethylpentane, and said at least one feed alkene is selected from the group consisting of pentene-1 and hexene-1.

8. A process in accordance with claim 1 wherein said effective alkylation conditions comprise a molar ratio of said at least one feed alkane to said at least one feed alkene in the range of about 6:1 to about 12:1 and a reaction temperature of about −20° C. to about 100° C.

9. A process in accordance with claim 8, wherein said effective alkylation conditions further comprise a liquid hourly space velocity of the feed comprising said at least one feed alkane and said at least one feed alkene of about 0.5–3 $cm^3$ feed per $cm^3$ catalyst composition per hour, a reaction temperature of about 0°–30° C., and a reaction pressure of about 2–8 atmospheres.

10. A process in accordance with claim 6 wherein said drying is carried out at a temperature of about 100°–150° C. for about 0.1–20 hours, and said calcining is carried out at a temperature of about 480–570 for about 2–6 hours.

11. A process in accordance with claim 1, comprising the additional step of separating said product alkanes boiling in a temperature range of about 310° F. to about 500° F. from at least one unconverted feed alkane and at least one unconverted feed alkene.

12. A process in accordance with claim 11, further comprising the additional step of separating said product alkanes boiling in a temperature range of about 310° F. to about 500° F. from said product hydrocarbons boiling at a temperature above 500° F.

13. A process in accordance with claim 11, wherein said separating is carried out by fractional distillation.

14. A process in accordance with claim 12, wherein said separating is carried out by fractional distillation.

15. A process for producing alkanes boiling in a temperature range of about 310° F. to about 500° F. at atmospheric pressure conditions which comprises contacting at least one feed alkane containing about 4-8 carbon atoms per molecule with at least one feed alkene containing about 4-6 carbon atoms per molecule in the presence of a catalyst composition which consists essentially of (a) trifluoromethanesulfonic acid and (b) a solid inorganic material consisting essentially of about 5-15 weight-% aluminum borate and aluminum oxide as the remainder, at effective alkylation conditions comprising a reaction temperature of about $-20°$ C. to about 100° C., so as to obtain at least one product alkane boiling at a temperature of about 310°-500° F. at atmospheric pressure conditions.

16. A process in accordance with claim 15, comprising the additional step of separating said at least one product alkane boiling at a temperature of about 310°-500° F. from unconverted feed alkanes.

17. A process in accordance with claim 16, further comprising the additional step of separating said at least one product alkane boiling at a temperature of about 310°-500° F. from by-product hydrocarbons boiling above a temperature of 500° F. at atmospheric pressure conditions.

18. A process in accordance with claim 17, wherein both separating steps are carried out by fractional distillation.

19. A process in accordance with claim 15, wherein said effective alkylation conditions comprise a reaction temperature of about 0° C. to about 30° C.

20. A process in accordance with claim 15, wherein said solid inorganic material contains 7-13 weight-% aluminum borate and about 87-93 weight-% aluminum oxide.

* * * * *